(12) United States Patent
West

(10) Patent No.: US 6,547,864 B1
(45) Date of Patent: Apr. 15, 2003

(54) ZINC OXIDE-DIMETHYLALKYLAMINE SALT WOOD PROTECTION COMPOSITION

(76) Inventor: Michael Howard West, 54 S. Crockett Rd., Senatobia, MS (US) 38668

( * ) Notice: Subject to any disclaimer, the term of this patent is extended or adjusted under 35 U.S.C. 154(b) by 0 days.

(21) Appl. No.: 10/238,058

(22) Filed: Sep. 10, 2002

(51) Int. Cl.⁷ .................................................. A01N 33/02
(52) U.S. Cl. ............................... 106/18.32; 106/18.36; 424/641; 514/663
(58) Field of Search ........................... 106/15.05, 18.32, 106/18.36; 424/641; 514/663

(56) References Cited

U.S. PATENT DOCUMENTS

| | | | | |
|---|---|---|---|---|
| 5,021,459 A | * | 6/1991 | Goettsche | 514/663 |
| 5,179,116 A | * | 1/1993 | Goettsche et al. | 514/388 |
| 5,186,947 A | * | 2/1993 | Goettsche et al. | 424/638 |
| 5,187,194 A | * | 2/1993 | Goettsche et al. | 514/499 |
| 5,880,143 A | * | 3/1999 | Goettsche et al. | 514/383 |
| 6,211,218 B1 | * | 4/2001 | Goettsche et al. | 514/383 |

FOREIGN PATENT DOCUMENTS

EP        147 976        *  7/1985

* cited by examiner

Primary Examiner—Anthony J. Green

(57) ABSTRACT

A composition for protecting wood from decay, mildew, sapstain, and ultraviolet light degradation which comprises zinc oxide in combination with dimethylalkylamine salts and monocarboxylic acids containing one to four carbons wherein the weight ratio of dimethylalkylamine salt to zinc oxide ranges from 1 to 10 to 10 to 1, and the stoichiometric ratio of monocarboxylic acid to zinc oxide ranges from 0.5 to 1.5.

3 Claims, No Drawings

ZINC OXIDE-DIMETHYLALKYLAMINE SALT WOOD PROTECTION COMPOSITION

CROSS REFERENCE TO RELATED APPLICATIONS

NOT APPLICABLE

STATEMENT REGARDING FEDERALLY SPONSORED RESEARCH OR DEVELOPMENT

NOT APPLICABLE

REFERENCE TO A MICROFICHE APPENDIX

NOT APPLICABLE

BACKGROUND OF THE INVENTION

The field of endeavor to which this invention pertains is the preparation and use of water dispersible zinc oxide dimethylalkylamine salt wood preservatives, sapstain control chemicals, and ultraviolet light inhibitors. The subject matter of the claimed invention relates to zinc oxide, dimethylalkylamines, and to monocarboxylic acids containing 1 to 4 carbons which react with dimethylalkylamines to form the dimethylalkylamine salt. Dimethylalkylamines are water insoluble while the dimethylalkylamine salts are water soluble.

Zinc oxide is well known wood protection chemical used in paints as well as in wood preservatives; it has found very little use as a sapstain control chemical. My invention relates to water borne zinc oxide; previously, zinc oxide has been combined with arsenic acid and ammonia for effective wood preservation. Now, with new restrictions on arsenic, these combinations will not be available for most wood protection applications. Dimethylakylamines and dimethylalkylamine salts have found some previous usage in wood protection, usually in combination with copper compounds. Monocarboxylic acids containing one to four carbons have been used as inert ingredients in wood preservative compositions.

My invention does not pertain to zinc oxide dissolved in water with ammonia or water soluble amines. It does not pertain to zinc oxide dissolved in organic solvents with petroleum soluble acids. It does pertain to zinc oxide, dimethylalkylamine salts, and monocarboxylic acids containing one to four carbons in wood protection compositions containing other fungicides, insecticides, and ultraviolet light inhibitors. The levels of monocarboxylic acid I teach are greater than that required to convert the added dimethylalkylamine to its salt.

To protect unseasoned wood from sapstain during short drying periods, the control chemical should remain on the surface of the wood. This requirement is best met by compositions of my invention which are less acidic. To penetrate and protect seasoned wood for extended periods of exterior exposure, the compositions of my invention should be more acidic.

BRIEF SUMMARY OF THE INVENTION

My invention teaches a composition for protecting wood from decay, mildew, sapstain, and ultraviolet light degradation which comprises zinc oxide in combination with dimethylalkyamine salts and monocarboxylic acids containing one to four carbons wherein the weight ratio of dimethyalkyllamine salt to zinc oxide ranges from 1 to 10 to 10 to 1, and the stoichiometric ratio of acid to zinc oxide ranges from 0.5 to 1.5. It is the object of my invention to provide improved wood protection with reduced levels of zinc oxide.

DETAILED DESCRIPTION OF THE INVENTION

The preferred embodiment of my invention relates to concentrate wood protection compositions prepared by blending zinc oxide first with a dimethylalkylamine, preferably dimethylcocoamine, then with a monocarboxylic acid containing one to four carbons, preferably propionic acid, and finally blending in any other desired fungicides, or insecticides. The addition of the acid results in an exothermic reaction forming the propionate salt of dimethylcocoamine, which in combination with the excess of propionic acid, forms a complex with the zinc oxide allowing it to disperse in water. Many composition according to my invention will require further acidification before they give a commercial level of penetration into seasoned wood when they are diluted with water. This acidification may occur in the concentrate or after dilution. It is preferred to occur after dilution, and can employ acids or acidic salts, and these may be formulated with other components.

Example 1 illustrates the preferred embodiment of my invention; this composition is a paste which exhibits slow liquid separation during periods of storage. The entire contents of the composition package should be washed with water into the wood treating holding tank. For sapstain protection my composition is ready to use at this point; for pressure treating the dispersion should be acidified to a molecular solution, as evidenced by change from a milky appearance to a clear solution. EXAMPLE 1:

| 99% zinc oxide | 20 pbw |
| 100% dimethylcocoamine | 40 pbw |
| 99% propionic acid | 40 pbw |

This composition was diluted with water to a 0.2% zinc oxide concentration and used to treat freshly cut mixed hardwood boards by dipping the boards for 30 seconds. These boards were then stacked for seasoning according to sawmill practice for six months. When the boards were properly seasoned they were planed and examined for blue stain. The boards treated with the composition of my invention exhibited much less staining than boards treated with the commercial chemical used by the sawmill.

The composition from Example 1 was also diluted with water to a 0.4% zinc oxide concentration, and the pH adjusted with propionic acid until the appearance changed from milky to clear. This solution was used to treat seasoned pine boards by a full cell process. These treated boards, and untreated controls, were exposed in partial tree shade, facing south at 45 degrees, for 2 years. After this exposure the treated boards evidenced no mildew, decay, or ultraviolet light degradation. The untreated controls were severely mildewed. there was softening from decay, and ultraviolet light degradation was visually evident.

I claim:

1. A composition for protecting wood from decay, mildew, sapstain, and ultraviolet light degradation which comprises zinc oxide in combination with dimethylalkylamine salts and monocarboxylic acids containing one to four carbons wherein the weight ratio of dimethylalkylamine salt to zinc oxide ranges from 1 to 10 to 10 to 1, and the stoichiometric ratio of monocarboxylic acid to zinc oxide ranges from 0.5 to 1.5.

2. A composition according to claim 1 which contains additional fungicides or insecticides.

3. A composition according to claim 1 which contains additional acidic salts.

* * * * *